(12) United States Patent
Padilla et al.

(10) Patent No.: US 7,531,561 B2
(45) Date of Patent: May 12, 2009

(54) GSK-3 INHIBITORS

(75) Inventors: Miguel Medina Padilla, Madrid (ES); Mercedes Alonso Cascón, Madrid (ES); Isabel Dorronsoro Díaz, Madrid (ES); Ana Martínez Gil, Madrid (ES); Gema Panizo del Pliego, Madrid (ES); Ana Fuertes Huerta, Madrid (ES); María José Pérez Puerto, Madrid (ES)

(73) Assignee: Noscira, S.A., Madrid (ES)

( * ) Notice: Subject to any disclaimer, the term of this patent is extended or adjusted under 35 U.S.C. 154(b) by 0 days.

(21) Appl. No.: 11/098,610

(22) Filed: Apr. 5, 2005

(65) Prior Publication Data

US 2005/0222220 A1 Oct. 6, 2005

(30) Foreign Application Priority Data

Apr. 5, 2004 (EP) .................................. 04075997

(51) Int. Cl.
*A61K 31/41* (2006.01)
*C07D 285/08* (2006.01)
(52) U.S. Cl. ...................... 514/361; 548/130
(58) Field of Classification Search ................. 548/130; 514/361
See application file for complete search history.

(56) References Cited

U.S. PATENT DOCUMENTS 6,872,737 B2 * 3/2005 Gil et al. ...................... 514/361

FOREIGN PATENT DOCUMENTS

WO WO 01/85685 11/2001

OTHER PUBLICATIONS

Martinez et al., J. Med. Chem., 2002, vol. 45, 1292-1299.*

Alonzo, M., et al., GSK-3 Inhibitors: Discoveries and Developments, Current Medical Chemistry, 11: 753-761, 2004.
Martinez, A., et al., Glycogen Synthase Kinase 3 (GSK-3) Inhibitors as New Promising Drugs . . . , Medicinal Research Reviews, 22(4): 1-12, 2002.
Martinez, A. et al., First Non-ATP Competitive Sythase . . . , J. Med. Chem., 45: 1292-1299, 2002.
Mª Mercedes Alonso Cascón, "Tesis Doctoral: Fármacos Modificadores De La Enfermedad De Alzheimer: 1,2,4-Tiadiazolidin-3,5-Dionas (TDZDs) Primeros Inhibidores ATP-NO Competitivos De GSK-3β," Universidad Autónoma De Madrid, 2003, chapters 1 and 5.

* cited by examiner

*Primary Examiner*—Rei-tsang Shiao
(74) *Attorney, Agent, or Firm*—King & Spalding, LLP; Kenneth H. Sonnenfeld; Michael A. Willis

(57) ABSTRACT

Provided are thiadiazolidine compounds of formula I

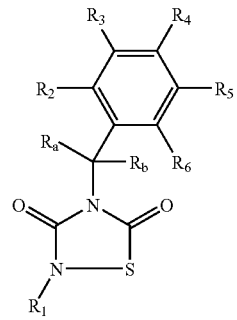

formula I wherein $R_1$ is an organic group having at least 8 atoms selected from C or O, which is not linked directly to the N through a —C(O)— and comprising at least an aromatic ring, and their pharmaceutical compositions. These compounds are selective GSK-3 inhibitors and have improved bioavailability. They are useful for the treatment of GSK-3 mediated diseases, among others Alzheimer's disease, type II diabetes, depression and brain injury.

27 Claims, No Drawings

GSK-3 INHIBITORS

FIELD OF THE INVENTION

The present invention relates to enzyme inhibitors, and more particularly to heterocyclic inhibitors of glycogen synthase kinase 3β, GSK-3, to processes of preparation of such compounds, to pharmaceutical compositions comprising them, and to their use for the treatment and or prophylaxis of a disease in which GSK-3 is involved, such as Alzheimer's disease or non-insulin dependent diabetes mellitus.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases. Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes (Coghlan et al., *Chemistry & Biology*, 7, 793-803 (2000); Kim and Kimmel, *Curr. Opinion Genetics Dev.*, 10, 508-514 (2000)). The threonine/serine kinase glycogen synthase kinase-3 (GSK-3) fulfills a pivotal role in various receptor-linked signalling pathways (Doble, B W, Woodgett, J R *J. Cell Sci.* 2003, 116:1175-1186). Dysregulation within these pathways is considered a crucial event in the development of several prevalent human disorders, such as type II diabetes (Kaidanovich O, Eldar-Finkelman H, *Expert Opin. Ther. Targets*, 2002, 6:555-561), Alzheimer's disease (Grimes C A, Jope R S, *Prog.Neurobiol.* 2001, 65:391-426), CNS disorders such as manic depressive disorder and neurodegenerative diseases, and chronic inflammatory disorders (Hoeflich K P, Luo J, Rubie E A, Tsao M S, Jin O, Woodgett J, *Nature* 2000, 406:86-90). These diseases may be caused by, or result in, the abnormal operation of certain cell signalling pathways in which GSK-3 plays a role.

GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

Currently, inhibition of GSK-3 may represent a viable strategy to develop novel medicinal entities for the treatment of such unmet diseases (Martinez A, Castro A, Dorronsoro I, Alonso M, *Med. Res. Rev.*, 2002, 22:373-384) through insulin mimicry, tau dephosphorylation and amyloid processing, or transcriptional modulation respectively.

Among the great diversity of chemical structures with GSK-3 inhibition already found (Dorronsoro, I; Castro, A; Martinez, A *Exp Opin Ther Patents* 2002, 12:1527-1536; Alonso, M. and Martinez, A. *Currrent Medicinal Chemistry* 2004, 11, 753-761), the 2,4-disubstituted thiadiazolidinone (TDZD) are presented as the first ATP-non competitive GSK-3 inhibitors (Martinez A, Alonso M, Castro A, Perez C, Moreno F, *J Med Chem*, 2002, 45:1292-1299; WO 01 85685 and U.S. 2003/0195238). These compounds have great interest since they are selective and do not show inhibition on other several kinases such as PKA, PKC, CK-2 and CDK1/cyclin B. However, thiadiazolidinones have the tendency to react with nucleophiles and this property may jeopardize their drug potential.

There is still a need to find good GSK-3 inhibitors, being both effective and selective, and having good "drugability" properties, i.e. good pharmaceutical properties related to administration, distribution, metabolism and excretion.

DESCRIPTION OF THE INVENTION

Taking advantage of some of our molecular modelling results and theories, we have designed and synthesized a second generation of 2,4-disubstituted thiadiazolidinones (TDZD) which are very stable against thiol-containing biological molecules such as glutathion and BSA (bovine serum albumina). Surprisingly, these compounds have also a very favourable drugable profile, in particular oral bioavailability and blood brain barrier penetration.

In one aspect the invention is directed to compounds of general formula I:

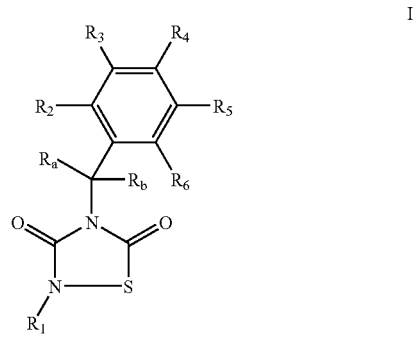

I wherein:

$R_1$ is an organic group having at least 8 atoms selected from C or O, which is not linked directly to the N through a —C(O)— and comprising at least an aromatic ring;

$R_a$, $R_b$, $R_2$, $R_3$, $R_4$, $R_5$, $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$_7$, —C(O)OR$_7$, —C(O)NR$_7$R$_8$ —C=NR$_7$, —CN, —OR$_7$, —OC(O)R$_7$, —S(O)$_t$—R$_7$, —NR$_7$R$_8$, —NR$_7$C(O)R$_8$, —NO$_2$, —N=CR$_7$R$_8$ or halogen, t is 0, 1, 2 or 3, $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

wherein $R_a$ and $R_b$ together can form a group =O, and wherein any pair $R_a R_2$, $R_2 R_3$, $R_3 R_4$, $R_4 R_5$, $R_5 R_6$, $R_6 R_b$, or $R_7 R_8$ can form together a cyclic substituent;

or a pharmaceutically acceptable salt, prodrug or solvate thereof.

We have found that compounds with a benzyl like structure at position 4 and a bulky group comprising an aromatic ring or rings at position 2 of the thiadiazolidinones interact optimally with the GSK-3 enzyme while at the same time presenting good drugability properties.

Preferred compounds are those in which $R_1$ has an aromatic group having at least 10 aromatic carbons. These compounds show good activity, stability and reduced binding to plasma proteins like glutatione and albumin.

Also preferred are compounds in which $R_1$ has an aromatic group directly linked to the N of the thiadiazolidine.

In a particular embodiment compounds in which $R_1$ is a naphthyl group are preferred, most preferably if $R_1$ is a α-naphthyl group.

Another preferred class of compounds are those in which the substituent at position 4 of the TDZD is an unsubstituted benzyl group.

In another aspect the invention is directed to pharmaceutical compositions which comprise a compound according to formula (I) or a pharmaceutically acceptable salt, prodrug or solvate thereof, and a pharmaceutically acceptable carrier, adjuvant or vehicle. In a preferred embodiment the formulation is oral.

The present invention is also directed to the use of the above defined compounds in the manufacture of a medicament, preferably for a GSK-3 mediated disease or condition.

Alternatively, the invention is also directed to a method of treatment of a GSK-3 mediated disease or condition comprising the administration of an effective amount of a compound of formula I as defined above, or a pharmaceutically acceptable salt, prodrug or solvate thereof, to a patient in need thereof.

In another aspect, the invention is directed to the use of the above defined compounds as reactives for biological assays, preferably as a reactive for GSK-3 inhibition.

In another aspect the invention is directed to a process for preparing a compound of formula I above by reaction of the appropriate benzyl isothiocyanate with a isocyanate of formula $R_1$—N=C=O.

DETAILED DESCRIPTION OF THE INVENTION

The typical compounds of this invention selectively inhibit GSK-3β without inhibition of other protein kinases such as PKA, PKC, CK-2 and CdK2, which could eliminate the effects. Additionally they do not bind significantly to model proteins such as Glutathione and Bovine Serum Albumin which is a good indication of their stability in plasma. They also show good absorption and blood brain barrier permeability as demonstrated by the examples.

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, carboxy, cyano, carbonyl, acyl, alkoxycarbonyl, amino, nitro, mercapto and alkylthio.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula —SRa where Ra is an alkyl radical as defined above, e.g., methylthio, ethylthio, propylthio, etc.

"Amino" refers to a radical of the formula —NH₂, —NHRa or —NRaRb, Wherein Ra and Rb are as defined above.

"Aryl" refers to a phenyl, naphthyl, indenyl, fenanthryl or anthracyl radical, preferably phenyl or naphthyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—$R_c$ and —C(O)-Rd where Rc is an alkyl radical as defined above and Rd is an aryl radical as defined above, e.g., acetyl, propionyl, benzoyl, and the like.

"Aroylalkyl" refers to an alkyl group substituted with —Ra—C(O)-Rd, wherein Ra is an alkyl radical. Preferred examples include benzoylmethyl.

"Carboxy" refers to a radical of the formula —C(O)OH.

"Cycloalkyl" refers to a stable 3-to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more such as alkyl, halo, hydroxy, amino, cyano, nitro, alkoxy, carboxy and alkoxycarbonyl.

"Fused aryl" refers to an aryl group, especially a phenyl or heteroaryl group, fused to another ring.

"Halo" refers to bromo, chloro, iodo or fluoro.

"Haloalkyl" refers to an alkyl radical, as defined above, that is substituted by one or more halo radicals, as defined above, e.g., trifluoromethyl, trichloromethyl, 2,2,2-trifluoroethyl, 1-fluoromethyl-2-fluoroethyl, and the like.

"Heterocycle" refers to a heterocyclyl radical. The heterocycle refers to a stable 3- to 15 membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, derivatives, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drugdesign and Discovery" Taylor & Francis (april 2002).

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

We have found that the compounds of formula I above are selective GSK-3 inhibitors (they do not show inhibition on other kinases) and additionally they present good pharmacological properties which makes them suitable for drug development. Indeed, through the adequate selection of the size and chemical characteristics of the substituents on the TDZD ring we have obtained compounds that are very stable against plasma molecules such as glutathion and BSA, and have shown good oral bioavailability and blood barrier penetration.

$R_1$ comprises an aromatic group, this improves the stability properties. In an embodiment $R_1$ has at least 10 aromatic carbons. Alternatively, good compounds are obtained with electron donating groups on the aromatic ring such as alkoxyl or methylendioxy.

Although $R_1$ can be linked to the TDZD through any group as long as it is not —C(O)— (because of degradation and poor stability in plasma), it is preferred that the aromatic group is directly linked to the N of the TDZD.

Representative substituents that can be used as $R_1$ are the following:

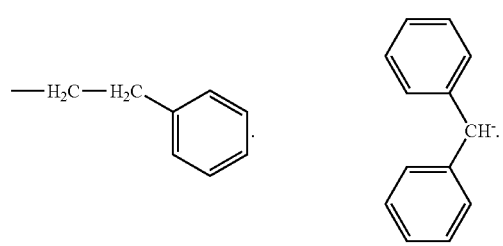

-continued

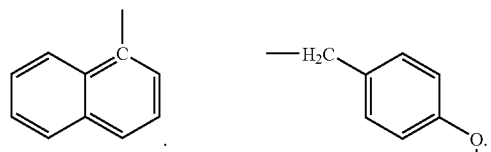

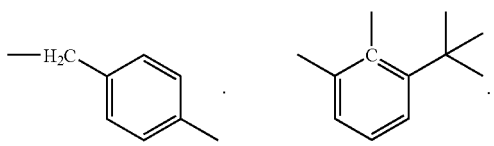

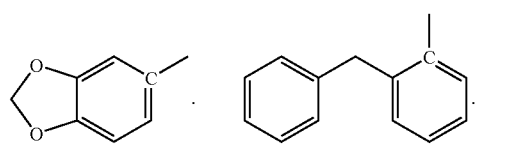

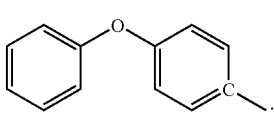

Very good results of stability and bioavailability in vivo have been obtained with a bulky aromatic group such as naphthyl. In particular alpha-naphthyl has given good results. When $R_1$ is alpha-naphthyl, it is preferred that it is an unsubstituted alpha-naphthyl.

Concerning the substituent at position 4 of the TDZD, it is preferred that $R_a$ and $R_b$ are H.

In another embodiment it is preferred that $R_2$, $R_3$, $R_4$, $R_5$, $R_6$ are independently selected from hydrogen, substituted or unsubstituted alkyl, $COR_7$, —C(O)OR$_7$, —OR$_7$, —NR$_7$R$_8$, or halogen.

Most preferably the substituent at position 4 is unsubstituted benzyl.

Representative compounds of the invention are the following:

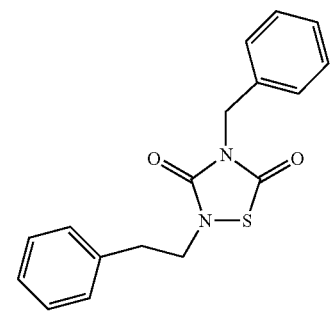

4-Benzyl-2-phenethyl-[1,2,4]thiadiazolidine-3,5-dione

-continued

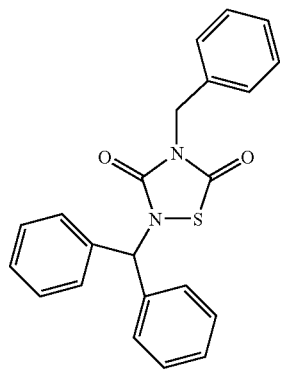

4-Benzyl-2-diphenylmethyl-1,2,4-thiadiazolidine-3,5-dione

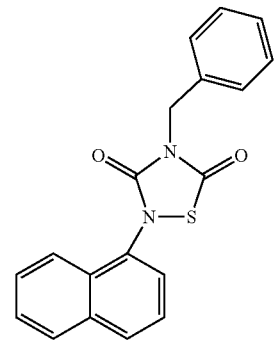

4-Benzyl-2-naphthalen-1-yl-[1,2,4]thiadiazolidine-3,5-dione

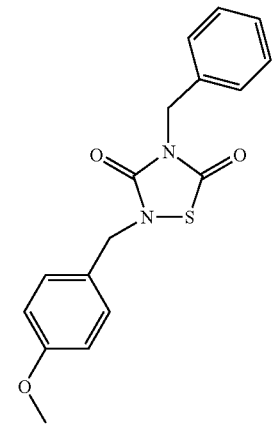

4-Benzyl-2-(4-methoxy-benzyl)-[1,2,4]thiadiazolidine-3,5-dione

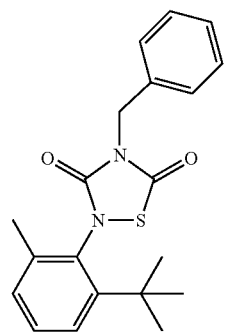

4-Benzyl-2-(2-tert-butyl-6-methyl-phenyl)-[1,2,4]thiadiazolidine-3,5-dione

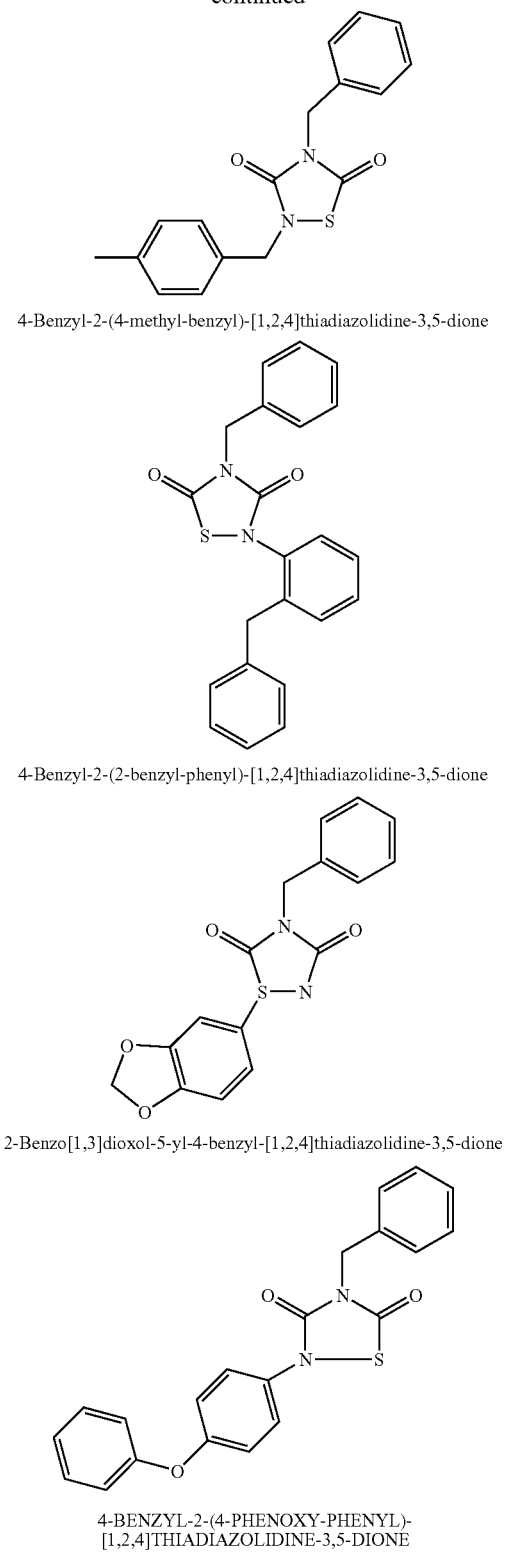

4-Benzyl-2-(4-methyl-benzyl)-[1,2,4]thiadiazolidine-3,5-dione

4-Benzyl-2-(2-benzyl-phenyl)-[1,2,4]thiadiazolidine-3,5-dione

2-Benzo[1,3]dioxol-5-yl-4-benzyl-[1,2,4]thiadiazolidine-3,5-dione

4-BENZYL-2-(4-PHENOXY-PHENYL)-
[1,2,4]THIADIAZOLIDINE-3,5-DIONE

And their salts, prodrugs and solvates.

The compounds of formula (I) defined above can be obtained by available synthetic procedures. Some examples of these procedures are described in WO 01/85685 and US 2003/0195238 and references therein. The content of these documents is incorporated herein by reference in its entirety.

Therefore in another aspect the invention provides a process for the preparation of a compound of formula (I) or a salt or solvate thereof as claimed in any of claims 1-11, which comprises reacting a benzyl substituted isothiocyanate of formula II

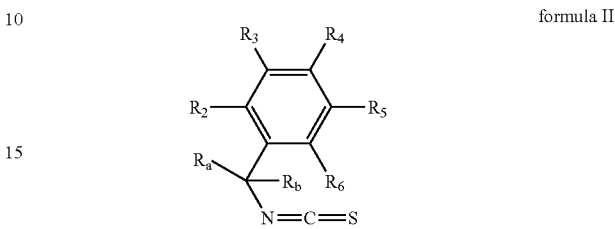

formula II with a compound of formula $R_1-N=C=O$.

For example, the following procedure can be used to produce 4-N-benzyl substituted thiadiazolidinones:

Scheme 1

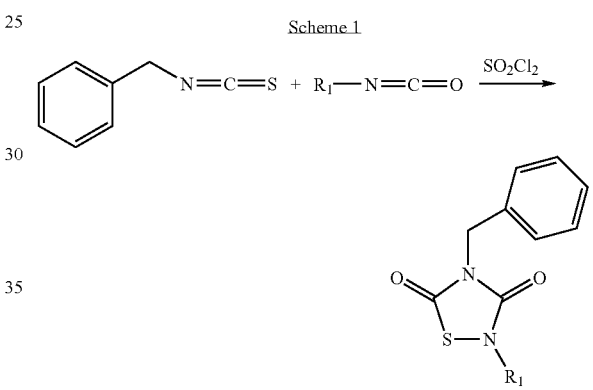

The general experimental procedure of Scheme 1 is described for example in Slomczynska, U.; Barany, G., "Efficient Synthesis of 1,2,4-Dithiazolidine-3,5-diones (Dithiasuccinoyl-amines) and observations on formation of 1,2,4-Thiadiazolidine-3,5-dione by related Chemistry", *J. Heterocyclic Chem.*, 1984, 21, 241-246.

For example, sulfuryl chloride is added dropwise with stirring, under nitrogen atmosphere, preferably at low temperature, preferably at about 5° C., to a solution of benzyl isothiocyanate and the isocyanate indicated in each case, in a suitable solvent such as hexane, ether or THF. When the addition is finished, the mixture is left to react, for example by stirring for 20 hours at room temperature. After this time, the resulting product is isolated by conventional methods such as suction filtration or solvent evaporation and then, the purification is performed (e.g. by recristallization or silica gel column chromatography using the appropriate eluent).

Other alternative procedures will be apparent to the person skilled in the art, such as the use of any other chlorinating agent instead of sulfuryl chloride, variations in the order of addition of the reactants and reaction conditions (solvents, temperature, etc).

The reaction products may, if desired, be purified by conventional methods, such as crystallisation, chromatography and trituration.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a GSK-3 mediated disease with a GSK-3 inhibitor as described above, which method comprises administering to a patient in need of such a treatment a therapeutically effective amount of a compound of formula (I) or a pharmaceutical composition thereof.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, brain injury, especially traumatic brain injury, cancer, leukopenia, Down's syndrome, Lewy body disease, inflammation, chronic inflammatory diseases, cancer and hyperproliferative diseases as hyperplasias and immunodeficiency.

In a particular embodiment of the invention the compounds of formula (I) or their pharmaceutical compositions, e.g. in oral form, are used for the treatment of the Alzheimer's disease.

In another embodiment of the invention the compounds of formula (I) or their pharmaceutical compositions, e.g. in oral form, are used for the treatment of the diabetes.

In another embodiment of the invention the compounds of formula (I) or their pharmaceutical compositions, e.g. in oral form, are used for the treatment of the depression.

In another embodiment of the invention the compounds of formula (I) or their pharmaceutical compositions, e.g. in oral form, are used for the treatment of brain injury.

The present invention further provides pharmaceutical compositions comprising a compound of this invention, pharmaceutically acceptable salts, derivatives, prodrugs or stereoisomers thereof with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form. Suitable dose forms for oral administration may be tablets and capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of many of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

In another aspect the invention relates to inhibiting GSK-3 activity in a biological sample with the compounds of formula (I), which method comprises contacting the biological sample with a GSK-3 inhibitor of formula (I). The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof. Thus, in one aspect the invention is directed to the use of compounds of formula I as reactives for biological assays, in particular as a reactive for GSK-3 inhibition.

The following examples are intended to further illustrate the invention. They should not be interpreted as a limitation of the scope of the invention as defined in the claims.

EXAMPLES

Synthesis of Compounds

General Experimental Procedure:

Sulfuryl chloride is added dropwise with stirring, under nitrogen atmosphere, at 5° C. to a solution of benzyl isothiocyanate and the isocyanate indicated in each case, in hexane, ether or THF. When the addition is finished, the mixture is stirred for 20 hours at room temperature. After this time, the resulting product is isolated by suction filtration or by solvent evaporation and then, the purification is performed by recristallization or silica gel column chromatography using the appropriate eluent. More details can be found in Slomczynska, U.; Barany, G., "Efficient Synthesis of 1,2,4-Dithiazolidine-3,5-diones (Dithiasuccinoyl-amines) and observations on formation of 1,2,4-Thiadiazolidine-3,5-dione by related Chemistry", *J. Heterocyclic Chem.*, 1984, 21, 241-246.

Example 1

2-Phenethyl-4-benzyl-(1,2,4)thiadiazolidine-3,5-dione (1)

Reagents: Benzyl-isothiocianate (6.5 mmol, 0.85 mL), phenethylisocyanate (6.5 mmol, 0.89 mL) and $SO_2Cl_2$ (6.5 mmol, 0.52 mL) in diethyl ether (25 mL). Isolation: solvent evaporation. Purification: silica gel column chromatography (AcOEt/hexane, 1:4).

Yield: 1.5 g (74%), yellow oil.

$^1$H-RMN (CDCl$_3$): 2.9 (t, 2H, CH$_2$CH$_2$Ph, J=7.2 Hz); 3.9 (t, 2H, CH$_2$CH$_2$Ph, J=7.2 Hz); 4.8 (s, 2H, CH$_2$Ph); 7.2-7.4 (m, 10H, arom)

$^{13}$C-RMN (CDCl$_3$): 34.9 (CH$_2$CH$_2$Ph); 4.9 (CH$_2$CH$_2$Ph); 46.2 (CH$_2$Ph); 126.9; 128.5; 128.6; 136.6 (C arom CH$_2$Ph); 128.1; 128.6; 128.6; 135.0 (C arom CH$_2$CH$_2$Ph); 152.6 (3-C=O); 165.6 (5-C=O).

Anal ($C_{17}H_{16}N_2O_2S$), C, H, N, S.

Example 2

4-Benzyl-2-naphthalen-1-yl-[1,2,4]thiadiazolidine-3,5-dione (2)

Reagents: Benzyl-isothiocianate (13 mmol, 1.72 mL), 1-naphthyl-isocyanate (13 mmol, 1.9 mL) and $SO_2Cl_2$ (13 mmol, 1.04 mL) in hexane (50 mL). Isolation: filtration of reaction mixture.

Purification: recrystallization from EtOH.

Yield: 3.8 g (87%), white needles. mp=150° C.

$^1$H-RMN (CDCl$_3$): 4.9 (s, 2H, CH$_2$Ph); 7.3-7.9 (m, 12H, arom.)

$^{13}$C-RMN (CDCl$_3$): 46.5 (CH$_2$Ph); 128.3; 128.6; 129.0; 135.0 (C arom, Ph); 122.0; 125.3; 126.8; 127.2; 127.5; 128.5; 130.8; 134.4 (C arom, naphthyl); 152.2 (3-C=O); 165.9 (5-C=O). Anal ($C_{19}H_{14}N_2O_2S$), C, H, N, S.

Example 3 (Comparative)

2-(1-adamantyl)-4-benzyl-[1,2,4]thiadiazolidine-3,5-dione (3)

Reagents: Benzylisothiocyanate (6.5 mmol, 0.85 mL), 1-Adamantyl-isocyanate (6.5 mmol, 1.15 g) and $SO_2Cl_2$ (6.5 mmol, 0.52 mL) in diethyl ether (25 mL). Isolation: solvent evaporation.

Purification: silica gel column chromatography (AcOEt/hexane, 1:4).

Yield: 0.89 g (40%), yellow crystals. mp=128.8° C.

$^1$H-RMN (CDCl$_3$): 1.7 (m, 6H, adamantyl); 2.2 (m, 3H, adamantyl); 2.3 (m, 6H, adamantyl); 4.8 (s, 2H, CH$_2$Ph); 7.2-7.4 (m, 5H, arom)

$^{13}$C-RMN (CDCl$_3$): 29.9; 30.0; 35.9; 41.0; 60.0 (C adamantyl); 45.3 (CH$_2$Ph); 127.8; 128.5; 128.6; 135.4 (C arom).

Anal. ($C_{19}H_{22}N_2O_2S$), C, H, N, S.

Example 4

4-Benzyl-2-(4-methyl-benzyl)-[1,2,4]thiadiazolidine-3,5-dione (4)

Reagents: Benzylisothiocyanate (6.5 mmol, 0.85 mL), 4-methylbenzyl-isocyanate (6.5 mmol, 0.90 mL) and $SO_2Cl_2$ (6.5 mmol, 0.52 mL) in diethyl ether (25 mL). Isolation: filtration of reaction mixture. Purification: recrystallization from MeOH.

Yield: 0.95 g (48%), white solid. mp=69.1° C.

$^1$H-RMN (CDCl$_3$): 2.4 (s, 3H, CH$_3$); 4.7 (s, 2H, CH$_2$-Ph); 4.8 (2H, s, CH$_2$-Ph); 7.2 (s, 4H, arom); 7.2-7.5 (m, 5H, arom).

$^{13}$C-RMN (CDCl$_3$): 21.3 (CH$_3$); 45.9 (CH$_2$Ph); 48.5 (CH$_2$Ph); 128.1; 128.6; 128.7; 135.0 (C arom); 128.4; 129.5; 131.1; 138.6 (C arom); 152.8 (3-C=O); 165.7 (5-C=O).

Anal. ($C_{17}H_{16}N_2O_2S$), C, H, N, S.

Example 5

4-Benzyl 2-((3,4-methylendioxy)phenyl)-[1,2,4]thiadiazolidine-3,5-dione (5)

Reagents: Benzylisothiocyanate (6.5 mmol, 0.85 mL), 3,4-(methylendioxy)phenyl-isocyanate (6.5 mmol, 1.06 mL) and $SO_2Cl_2$ (6.5 mmol, 0.52 mL) in diethyl ether (25 mL). Isolation: filtration of reaction mixture. Purification: recrystallization from MeOH.

Yield: 1.4 g (66%), white solid. mp=126.5° C.

$^1$H-RMN (CDCl$_3$): 4.9 (s, 2H, CH$_2$Ph); 6.0 (s, 2H, O—CH$_2$—O); 6.7-7.0 (m, 3H, arom); 7.3-7.5 (m, 5H, arom)

$^{13}$C-RMN (CDCl$_3$): 46.2 (CH$_2$Ph); 128.2; 128.6; 129.0; 134.9 (C arom); 101.8 (O—CH$_2$—O); 106.4; 108.3; 118.2; 129.0; 148.1; 146.8 (C arom); 151.2 (3-C=O); 164.9 (5-C=O) Anal. ($C_{16}H_{12}N_2O_4S$), C, H, N, S.

Example 6

4-Benzyl-2-diphenylmethyl-1,2,4-thiadiazolidine-3,5-dione (6)

Reagents: Benzylisothiocyanate (6.5 mmol, 0.85 mL), diphenylmethyl-isocyanate (6.5 mmol, 1.23 mL) and $SO_2Cl_2$ (6.5 mmol, 0.52 mL) in diethyl ether (25 mL). Isolation: filtration of reaction mixture. Purification: recrystallization from MeOH.

Yield: 1.79 g (80%), white solid. mp=111.5° C.

$^1$H-RMN (CDCl$_3$): 4.85 (s, 2H, CH$_2$Ph); 6.8 (s, 1H, Ph-CH-Ph); 7.2-7.4 (m, 15H, arom)

$^{13}$C-RMN (CDCl$_3$): 45.9 (CH$_2$Ph); 61.6 (Ph-CH-Ph); 128.0; 128.6; 128.7; 135.0 (C arom); 128.1; 128.5; 128.5; 137.5 (2×Ph); 152.6 (3-C=O); 165.8 (5-C=O) Anal. ($C_{22}H_{18}N_2O_2S$), C, H, N, S.

Example 7

4-Benzyl-2-(4-metoxybenzyl)-[1,2,4]thiadiazolidine-3,5-dione (7)

Reagents: Benzylisothiocyanate (6.5 mmol, 0.85 mL), p-metoxybenzyl-isocyanate (6.5 mmol, 0.92 mL) and $SO_2Cl_2$ (6.5 mmol, 0.52 mL) in diethyl ether (25 mL). Isolation: solvent evaporation. Purification: silica gel column chromatography (AcOEt/hexane, 1:4).

Yield: 1.30 g (61%), yellowish solid. mp=86.4° C.

$^1$H-RMN (CDCl$_3$): 3.8 (s, 3H, CH$_3$); 4.7 (s, 2H, CH$_2$-Ph-OMe); 4.8(s, 2H, CH$_2$-Ph); 7.2-7.4 (m, 5H, arom); 6.8 (d, 2H, J=8.6 Hz); 7.2 (d, 2H, J=8.6 Hz)(Arom)

$^{13}$C-RMN (CDCl$_3$): 45.9 (CH$_2$-Ph); 48.2 (CH$_2$-Ph-OMe); 55.2 (O—CH$_3$); 128.0; 129.8; 128.4; 135.0 (C arom-Ph);

126.2; 128.5; 114.2; 159.7 (C arom Ph-OMe); 152.7 (3-C=O); 165.6 (5-C=O).

Anal. ($C_{17}H_{13}N_2O_3S$), C, H, N, S.

Example 8

4-Benzyl-2-(2-tert-butyl-6-methyl-phenyl)-(1,2,4)thiadiazolidine-3,5-dione (8)

Reagents: Benzylisothiocyanate (3.5 mmol, 0.45 mL), 2-tert-butyl-6-methylisocyanate (3.5 mmol, 662.5 mg) and $SO_2Cl_2$ (3.5 mmol, 0.25 mL) in diethyl ether (15 mL). Isolation: solvent evaporation. Purification: silica gel colum chromatography (AcOEt/hexane, 1:10). Yield: 0.17 g (14%), brown solid. mp=89.8° C.

$^1$H-RMN (CDCl$_3$): 1.4 (s, 9H, C(CH$_3$)$_3$); 2.1 (s, 3H, CH$_3$); 4.9 (2d, 2H, CH$_2$-Ph, J=6.3 Hz); 7.1-7.5 (m, 8H, arom)

$^{13}$C-RMN (CDCl$_3$): 17.8 (CH$_3$); 31.9 (C(CH$_3$)); 35.9 (C(CH$_3$)); 46.2 (CH$_2$-Ph); 126.1; 128.6; 128.5; 135.1 (C arom-Bn); 131.5; 150.4; 139.4; 128.1; 129.5; 129.9 (C arom-Ph); 152.4 (3-C=O); 165.7 (5-C=O)

Anal. ($C_{20}H_{22}N_2O_2S$), C, H, N, S.

Example 9

4-Benzyl-2-(2-benzyl-phenyl)-[1,2,4]thiadiazolidine-3,5-dione (9)

Reagents: Benzylisothiocyanate (6.5 mmol, 0.85 mL), 2-benzylphenyl-isocyanate (6.5 mmol, 0.82 mL) and $SO_2Cl_2$ (6.5 mmol, 0.5 mL) in diethyl ether (25 mL). Isolation: filtration of reaction mixture. Purification: recrystallization from EtOH Yield: 1.50 g (62%), white solid. mp=154.9° C.

$^1$H-RMN (CDCl$_3$): 3.9 (s, 2H, Ph-CH$_2$-Ph); 4.86 (s, 2H, CH$_2$Ph); 6.9-7.5 (m, 14H, arom)

$^{13}$C-RMN (CDCl$_3$): 38.1 (Ph-CH$_2$-Ph); 46.1(CH$_2$-Ph); 135.1; 128.5; 128.6; 129.2 (C-Bn); 138.9; 129.9; 131.6; 128.4; 127.9; 133.1 (Ph-CH$_2$-Ph); 140.9; 128.7; 128.6; 126.4 (Ph-CH$_2$-Ph); 151.2 (3-C=O); 166.0 (5-C=O)

Anal. ($C_{22}H_{18}N_2O_2S$), C, H, N, S.

Example 10

4-Benzyl-2-(4-phenoxyphenyl)-[1,2,4]thiadiazolidine-3,5-dione (10)

Reagents: Benzylisothiocyanate (13 mmol, 1.6 mL), 4-phenoxyphenyl-isocyanate (13 mmol, 2.3 mL) and $SO_2Cl_2$ (13 mmol, 1 mL) in diethyl ether (50 mL). Isolation: filtration of reaction mixture. Purification: recrystallization from EtOH.

Yield: 4.12 g (84%), white solid. mp=88.8° C.

$^1$H-RMN (CDCl$_3$): 4.92 (s, 2H, CH$_2$Ph); 7.0-7.6 (m, 14H, arom)

$^{13}$C-RMN (CDCl$_3$): 46.1 (CH$_2$Ph); 134.9; 128.7; 129.1; 128.3 (CH$_2$-Ph); 130.1; 125.7; 119.2; 156.3 (Ph-O-Ph); 156.3; 119.1; 129.8; 123.8 (Ph-O-Ph); 151.1 (3-C=O); 165.0 (5-C=O) Anal. ($C_{21}H_{16}N_2O_3S$), C, H, N, S.

Biological Methods

Example 11

GSK-3β Inhibition

The GSK-3β activity was determined by incubation of a mixture of recombinant human GSK-3 enzyme, a phosphate source and GSK-3 substrate in the presence and in the absence of the corresponding test compound, and by measuring the GSK-3 activity of this mixture.

Recombinant human glycogen synthase kinase 3β was assayed in MOPS 8 mM pH 7.3, EDTA 0.2 mM, MgCl$_2$ 10 mM and sodium orthovanadate 0.25 mM in the presence of 62.5 μM of Phospho-Glycogen Synthase Peptide-2 (GS-2), 0.5 μCi γ-$^{33}$P-ATP and unlabelled ATP at a final concentration of 12.5 μM. The final assay volume was 20 μl. After incubation for 30 minutes at 30° C., 15 μl aliquots were spotted onto P81 phosphocellulose papers. Filters were washed four times for at least 10 minutes each and counted with 1.5 ml of scintillation cocktail in a scintillation counter.

The compounds IC$_{50}$ values were calculated analyzing inhibition curves by non-linear regression using GraphPad Prism.

The IC$_{50}$ (concentration at which 50% of enzyme inhibition is shown) values are gathered in table 1.

TABLE 1

IC$_{50}$ values

| Comp. | R$_1$ | IC$_{50}$ GSK-3 (μM) |
|---|---|---|
| 1 | —H$_2$C—H$_2$C—(phenyl) | 3 |
| 2 | 1-naphthyl | 2.4 |
| 3 (comparative) | adamantyl | 50 |
| 4 | —H$_2$C—(4-methylphenyl) | 1.8 |
| 5 | benzo[1,3]dioxol-5-yl | 4.2 |

TABLE 1-continued

IC$_{50}$ values

[structure: 2-R$_1$-substituted thiadiazolidine-3,5-dione with N-benzyl]

| Comp. | R$_1$ | IC$_{50}$ GSK-3 (μM) |
|---|---|---|
| 6 | diphenylmethyl (CH-) | 2 |
| 7 | —H$_2$C—C$_6$H$_4$—OCH$_3$ | <50 |
| 8 | 2-tert-butyl-6-methylphenyl | 3 |
| 9 | 2-(phenylmethyl)phenyl | 8 |
| 10 | 4-phenoxyphenyl | 3 |

Example 12

Binding to GSH and BSA

Sample Preparation

The compound (working solution at 1 mM) were incubated during 30 minutes at room temperature with Glutathione (Sigma) and Bovine serum albumin (Fraction V) (Sigma) at equimolecular concentrations (1 mM). After this time the solution was filtrated and analysed by HPLC-UV/MS.

Chromatographic Methods

HPLC was performed with a symmetry C18 (2.1×150 mm, 3.5 μm) column using a Waters Alliance 2695 with a 2996 photodiode array and ZQ2000 mass spectrometer used for the analytical separation and for UV and mass determination. The gradient used for the elution was:

| TIME (MIN) | % A | % B |
|---|---|---|
| 0 | 100 | 0 |
| 20 | 0 | 100 |
| 21 | 100 | 0 |
| 25 | 100 | 0 |

Flux: 0.25 mL/min; temp: 30° C.; Detection: 250 nm; Injection Volumen: 10 μL

Results are collected in Table 2

TABLE 2

| | % UNBINDING COMPOUND | |
|---|---|---|
| Compound | GLUTATHIONE | ALBUMIN |
| 1 | 34.7 | 80.2 |
| 2 | 95.0 | 98.0 |
| 3 (COMPARATIVE) | 15.0 | 54.0 |
| 4 | 32.3 | 67.2 |
| 5 | 72.0 | 65.5 |
| 6 | 52.0 | 84.0 |
| 7 | 31.0 | 68.3 |
| 8 | 59.4 | 62.3 |
| 9 | 71.7 | 91.4 |
| 10 | 100.0 | 98.9 |

The table clearly indicates that all the compounds except compound 3 which has no aromatic ring have at least in one of the two properties assayed more than 50% of unbinding compound. There are also some compounds with more than 70% of unbinding compounds in the two assays. The presence of an aromatic group at position 2 (R$_1$) of the TDZD clearly improves the properties of these compounds. This effect is bigger if there are at least 10 aromatic carbons present in the substituent, or electrondonating substituents such as in compounds 5 and 10. We can also observe that when the aromatic group is directly linked to the N of the TDZD the results are better. Best results were obtained with phenyloxyphenyl and with alpha-naphthyl.

These data are clearly better than those of previous TDZD compounds. Indeed, previously described 2,4-dibenzyl-1,2,4-thiadiazolidine-3,5-dione with a smaller substituent at position 2 of the thiadiazolidinone gives a value of 17.1% in the glutathione assay and 57.0% in the albumin assay, much lower than for example present compound 4 which has an additional methyl group, and in the range of comparative example 3 which has no aromatic rings. And the compound with R$_1$=benzoyl decomposes during the assays thus performing much worse than the compounds of formula I.

Example 13

Brain Permeation After Oral and Intravenous Administration

This study was conducted at CIDA S.A.L., Sta Perpétua de Mogola (Barcelona) Spain.

The objective of this study was investigate the pharmacokinetic behaviour of compound 2 (R$_1$=alpha-naphthyl) and its possible accumulation in the brain tissue after both oral and intravenous administration.

C57/BL6 mice (15-30 g) from Charles River laboratories Spain were used in this study. All the mice had free access to the dried, pelleted standard mouse diet. Water was available ad libitum. Animals were fasted for 4 hours before treatment, but with water ad libitum. They were fed 2 hours after administration.

Compound 2 was formulated in 10.0% PEG400, 10.0% Cremophor in bidistilled water. The route of administration was a single oral administration at 20 g/kg (10 mL/kg) and single intravenous administration at 2 mg/kg (10 mL/kg). An additional experiment was performed at 200 mg/kg by the oral route only to determine proportionality of absorption.

Four animals (2 males and 2 females) were used at each extraction time. Blood was heparinised, and after centrifugation (3000 rpm, 10 mins, 5° C.), two plasma aliquots stored at −20° C. and −30° C. until analysis (HPLC/MS-MS).

The summary of the experiment results is showed in the table 3.

TABLE 3

| Dose | 200 mg/kg | 20 mg/kg |
| --- | --- | --- |
| C max | 9061.34 ng/mL | 904.95 ng/mL |
| Bioavailability | Not evaluated | 31.87% |

Compound 2 is quickly absorbed from the GI tract after oral administration. A half-life of 6 hours was found after an oral administration of 20 mg/kg. Compound 2 presented a bioavailability of 31.87%. Levels of Compound 2 were detected in the brain, both after oral and intravenous administration. This shows that compounds of formula I above have good bioavailability properties and are suitable for development as a drug for the treatment of GSK-3 mediated diseases or conditions.

The invention claimed is:

1. A compound of general formula (I)

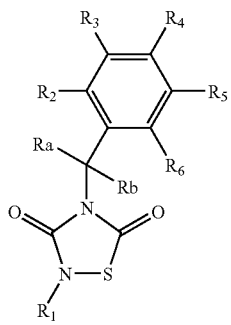

formula I wherein:

$R_1$ is a group selected from the group consisting of:

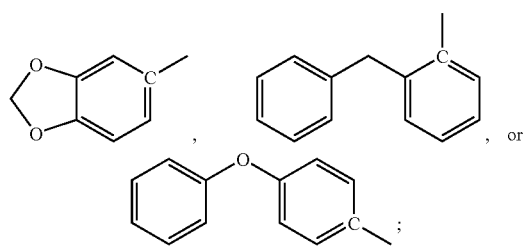

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$_7$, —C(O)OR$_7$, —C(O)NR$_7$R$_8$, —C=NR$_7$, —CN, —OR$_7$, —OC(O)R$_7$, —S(O)$_t$—R$_7$, —NR$_7$R$_8$, —NR$_7$C(O)R$_8$, —NO$_2$, —N=CR$_7$R$_8$ or halogen, t is 0, 1, 2 or 3, $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt, or prodrug thereof.

2. A compound according to claim 1 wherein both $R_a$ and $R_b$ are H.

3. A compound according to claim 1 wherein $R_2$, $R_3$, $R_4$, $R_5$, and $R_6$ are independently selected from hydrogen, substituted or unsubstituted alkyl, —COR$_7$, C(O) OR$_7$,—OR$_7$, —NR$_7$R$_8$, or halogen, wherein $R_7$ and $R_8$, are as defined in claim 1.

4. A compound according to claim 1 wherein $R_2$, $R_3$, $R_4$, $R_5$, and $R_6$ are H.

5. A compound according to claim 1 which has the formula:

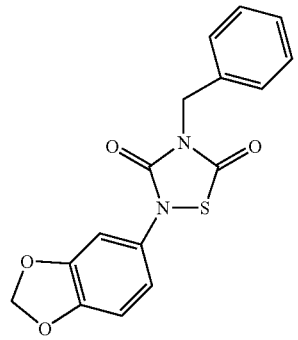

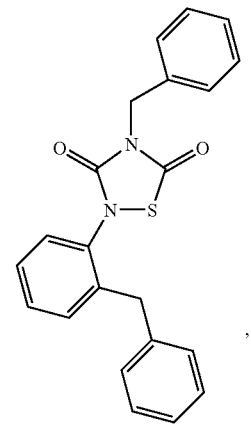

, or

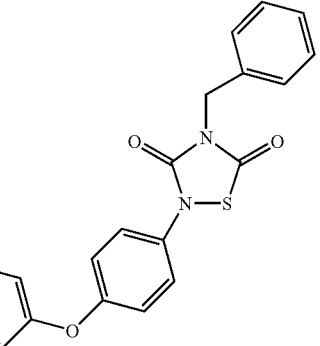

or a pharmaceutically acceptable salt, or prodrug thereof.

6. A process for the preparation of a compound of formula (I) or a salt thereof as claimed in claim 1, which comprises reacting a benzyl substituted isothiocyanate of formula II

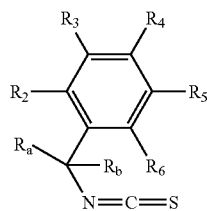

formula II with a compound of formula $R_1$—N=C=O.

7. A process according to claim 6, which comprises the reaction:

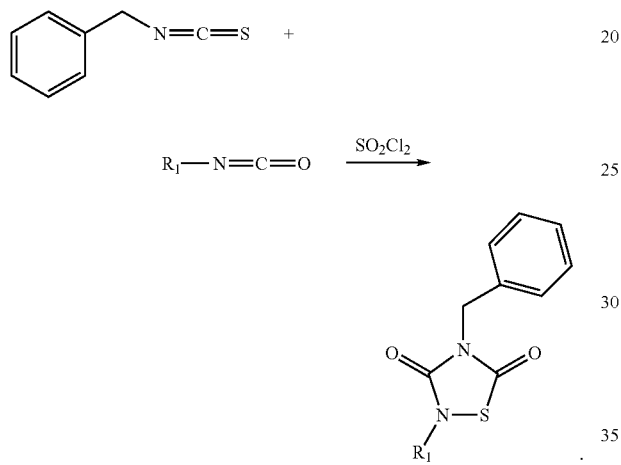

8. A pharmaceutical composition which comprises a compound as claimed in claim 1 or a pharmaceutically acceptable salt, or prodrug thereof and a pharmaceutically acceptable carrier, adjuvant or vehicle.

9. A pharmaceutical composition according to claim 8, wherein the pharmaceutical composition is formulated for oral administration.

10. A compound according to claim 1 which has the formula:

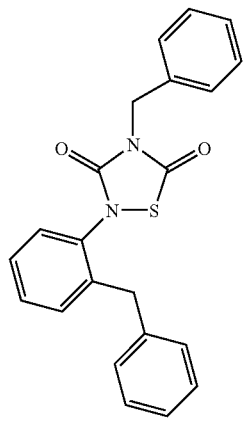

11. A compound according to claim 1 which has the formula:

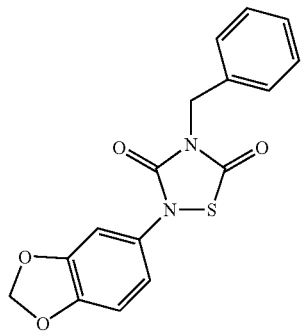

12. A compound according to claim 1 which has the formula:

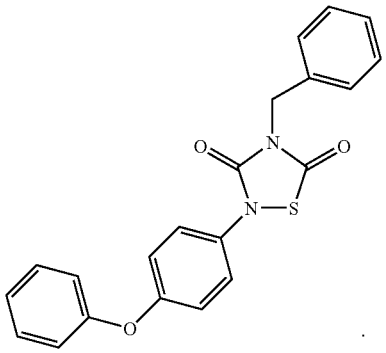

13. A compound of general formula (I)

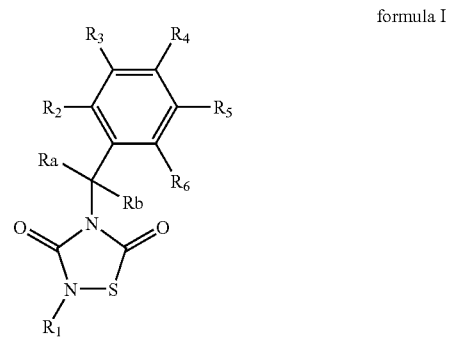

formula I wherein:

$R_1$ is a group selected from the group consisting of:

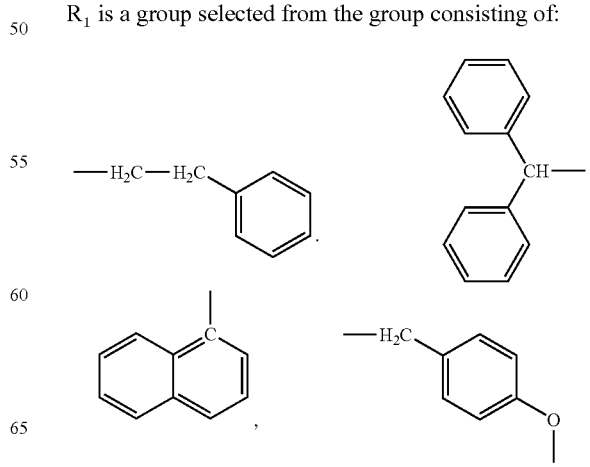

-continued

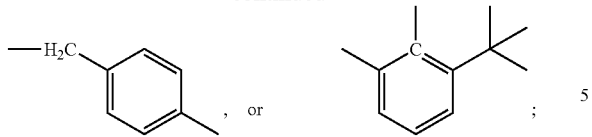, or ;

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_7$, —C(O) $OR_7$, —$C(O)NR_7R_8$, —C=$NR_7$, —CN, —$OR_7$, —$OC(O)R_7$, —$S(O)_t$—$R_7$, —$NR_7R_8$, —$NR_7C(O)R_8$, —$NO_2$, —N=$CR_7R8$ or halogen, t is 0,1,2 or 3, $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt, or prodrug thereof.

14. A compound according to claim 13, wherein both $R_a$ and $R_b$ are H.

15. A compound according to claim 13,1 wherein $R_2$, $R_3$, $R_4$, $R_5$, and $R_6$ are independently selected from hydrogen, substituted or unsubstituted alkyl, —$COR_7$, —C(O) $OR_7$, —$OR_7$, —$NR_7R_8$, or halogen.

16. A compound according to claim 13, wherein $R_2$, $R_3$, $R_4$, $R_5$, and $R_6$ are H.

17. A compound according to claim 13, which has the formula:

-continued

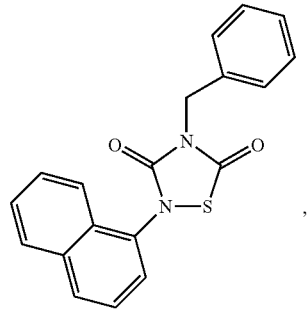,

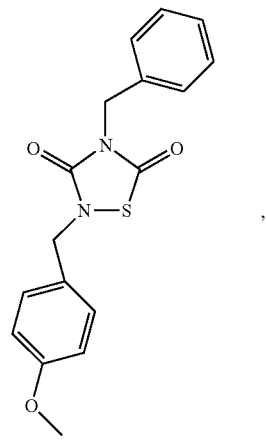,

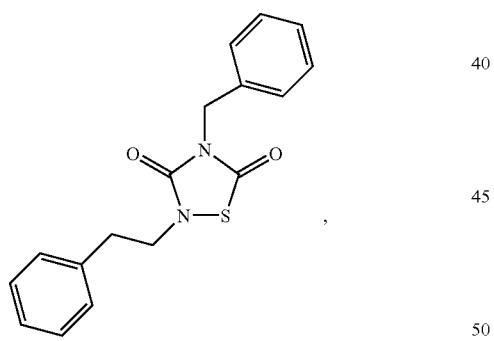,

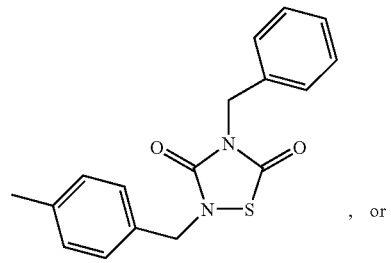, or

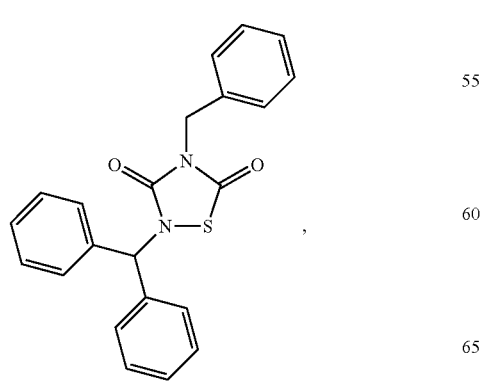,

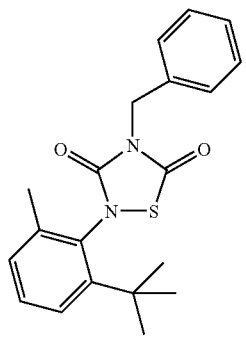, or a pharmaceutically acceptable salt, or prodrug thereof.

18. A process for the preparation of a compound of formula (I) or a salt thereof as claimed in claim 13, which comprises reacting a benzyl substituted isothiocyanate of formula II

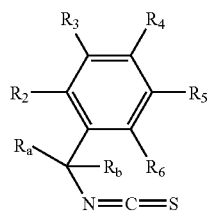

formula II with a compound of formula $R_1\text{-}N{=}C{=}O$.

19. A process according to claim 18, which comprises the reaction:

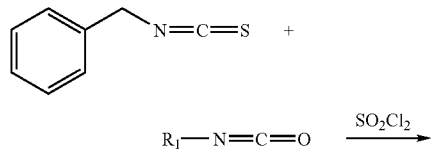

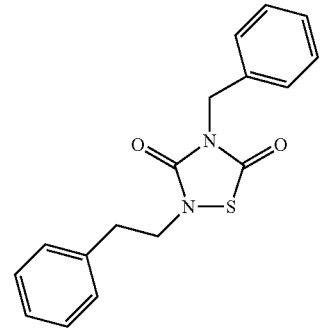

20. A pharmaceutical composition which comprises a compound as claimed in claim 13 or a pharmaceutically acceptable salt, or prodrug thereof and a pharmaceutically acceptable carrier, adjuvant or vehicle.

21. A pharmaceutical composition according to claim 20, wherein the pharmaceutical composition is formulated for oral administration.

22. A compound according to claim 13 which has the formula:

23. A compound according to claim 13 which has the formula:

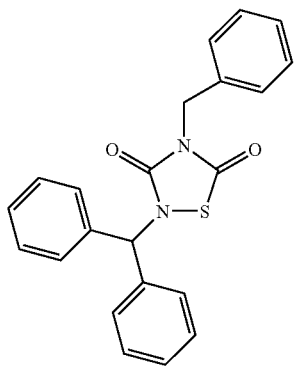

24. A compound according to claim 13 which has the formula:

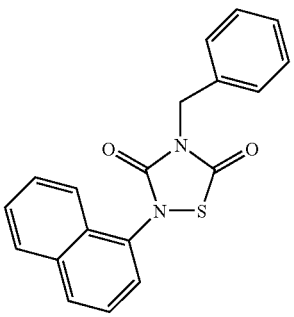

25. A compound according to claim 13 which has the formula:

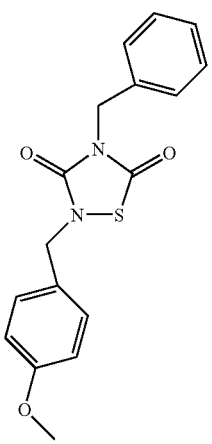

26. A compound according to claim 13 which has the formula:
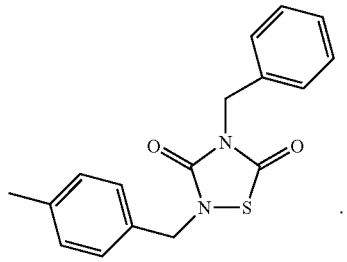
27. A compound according to claim 13 which has the formula:
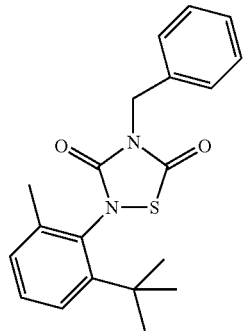
* * * * *

UNITED STATES PATENT AND TRADEMARK OFFICE
CERTIFICATE OF CORRECTION

PATENT NO. : 7,531,561 B2
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

Column 2, line 21, please amend "glutathion" to --glutathione--;

Column 2, line 47, please amend "$R_a$, $R_b$, $R_1$, $R_2$, $R_3$, $R_4$, $R_5$, $R_6$" to --$R_a$, $R_b$, $R_1$, $R_2$, $R_3$, $R_4$, $R_5$, and $R_6$--;

Column 3, line 7, please amend "glutatione" to --glutathione--;

Column 6, line 42, please amend "glutathion" to --glutathione--;

Column 6, lines 56-67, please delete the extra periods and amend

" 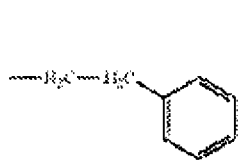 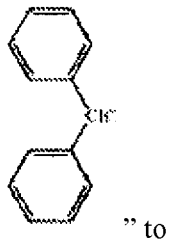 " to

-- 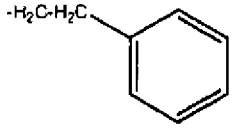 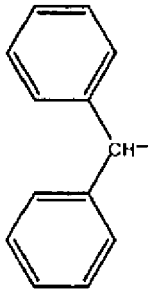 --;

UNITED STATES PATENT AND TRADEMARK OFFICE
CERTIFICATE OF CORRECTION

PATENT NO. : 7,531,561 B2  
APPLICATION NO. : 11/098610  
DATED : May 12, 2009  
INVENTOR(S) : Miguel Medina Padilla et al.

It is certified that error appears in the above-identified patent and that said Letters Patent is hereby corrected as shown below:

Column 7, lines 5-30, please delete the extra periods and amend

"
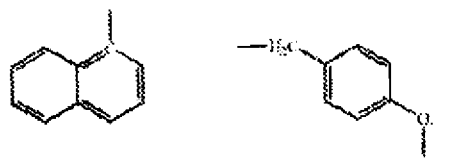

" to

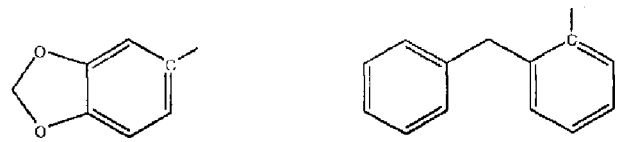 or

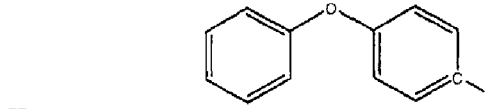 . --;

UNITED STATES PATENT AND TRADEMARK OFFICE
CERTIFICATE OF CORRECTION

PATENT NO. : 7,531,561 B2
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

Column 7, lines 41-42, please amend "$R_2, R_3, R_4, R_5, R_6$" to --$R_2, R_3, R_4, R_5,$ and $R_6$--;

Column 9, lines 33-44, please amend the chemical drawing

"
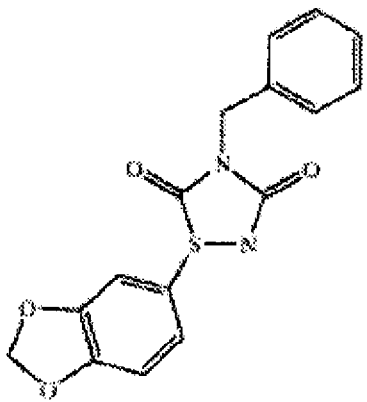
"

to

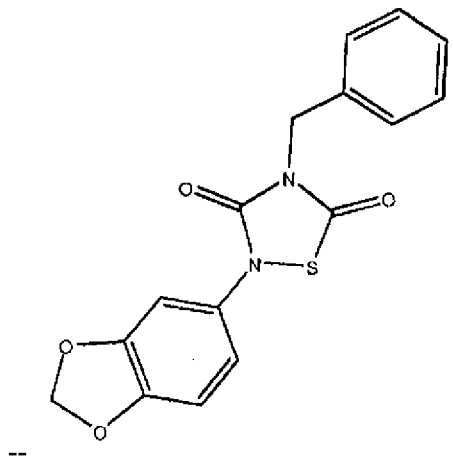
--;

Column 9, line 64, please amend "And their salts" to --and their salts--;

UNITED STATES PATENT AND TRADEMARK OFFICE
CERTIFICATE OF CORRECTION

PATENT NO. : 7,531,561 B2  Page 4 of 7
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

Column 10, line 5, please amend "as claimed in any of claims 1-11" to --as described herein--;

Column 16, lines 49-55, please amend

"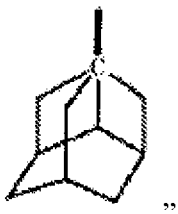"

to

--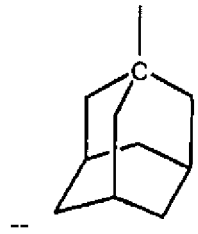--;

Column 20, claim 3, lines 10-11, please amend "-COR$_7$, C(O) OR$_7$,-OR$_7$, -NR$_7$,R$_8$" to -- -COR$_7$, C(O)OR$_7$, -OR$_7$, -NR$_7$R$_8$--;

Column 20, claim 5, lines 50-63, please delete the extra period by amending

"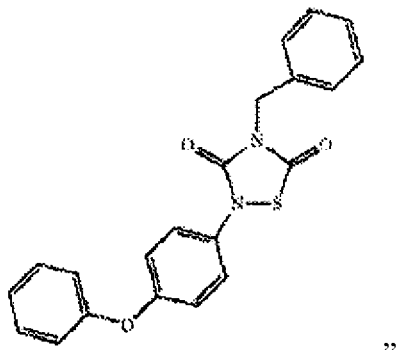"

UNITED STATES PATENT AND TRADEMARK OFFICE
CERTIFICATE OF CORRECTION

PATENT NO. : 7,531,561 B2
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

to

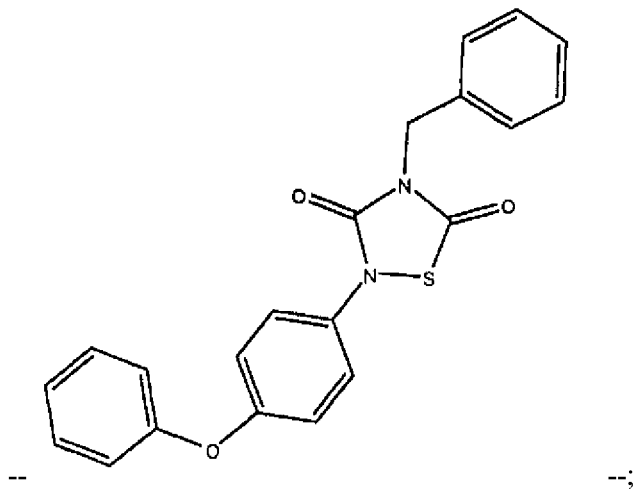

--                                                              --;

Column 22, claim 13, lines 55-65, please convert the extra periods to commas by amending "
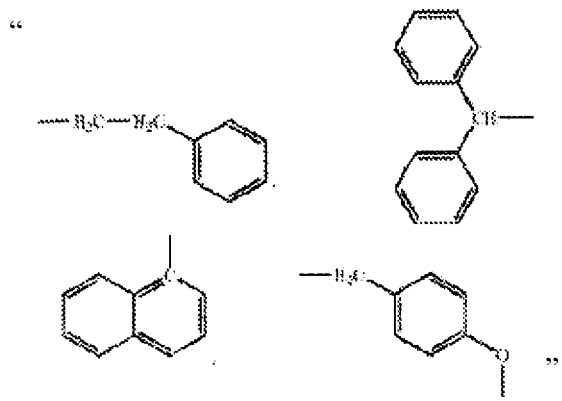
"

to

UNITED STATES PATENT AND TRADEMARK OFFICE
CERTIFICATE OF CORRECTION

PATENT NO. : 7,531,561 B2
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

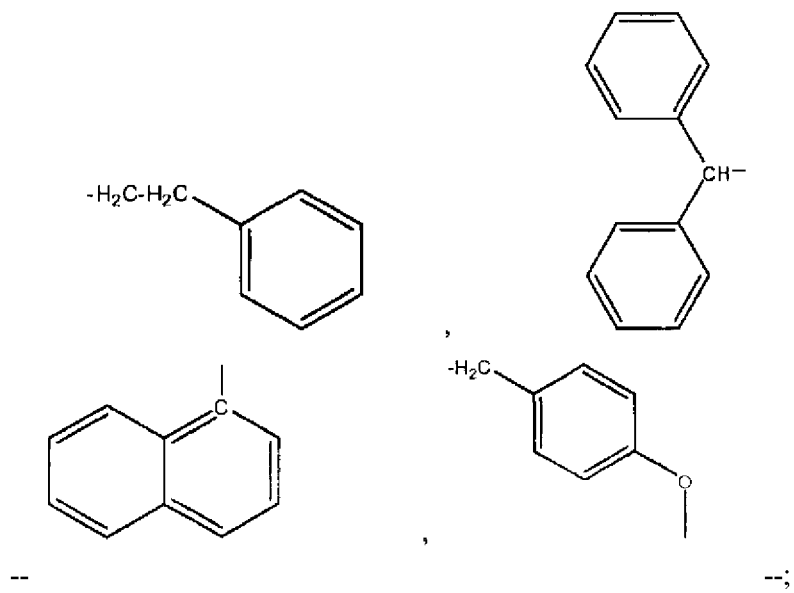

Column 23, claim 13, lines 14-17, please amend

"-C(O) $OR_7$, -C(O)$NR_7R_8$, -C=$NR_7$, -CN, -$OR_7$, -OC(O)$R_7$, -S(O)$_t$-$R_7$, -$NR_7R_8$, -$NR_7$C(O)$R_8$, -$NO_2$, -N=$CR_7R8$ or halogen, t is 0,1,2 or3"

to

-- -C(O)$OR_7$, -C(O)$NR_7R_8$, -C=$NR_7$, -CN, -$OR_7$, -OC(O)$R_7$, -S(O)$_t$-$R_7$, -$NR_7R_8$, -$NR_7$C(O)$R_8$, -$NO_2$, -N=$CR_7R_8$ or halogen, t is 0,1,2 or 3--;

Column 23, claim 15, line 28, please amend "claim 13,1 wherein" to --claim 13, wherein--;

UNITED STATES PATENT AND TRADEMARK OFFICE
CERTIFICATE OF CORRECTION

PATENT NO. : 7,531,561 B2
APPLICATION NO. : 11/098610
DATED : May 12, 2009
INVENTOR(S) : Miguel Medina Padilla et al.

It is certified that error appears in the above-identified patent and that said Letters Patent is hereby corrected as shown below:

Column 23, claim 15, line 30, please amend "-C(O) OR$_7$" to --C(O)OR$_7$--.

Signed and Sealed this

Thirteenth Day of October, 2009

David J. Kappos
*Director of the United States Patent and Trademark Office*